Figure 1:
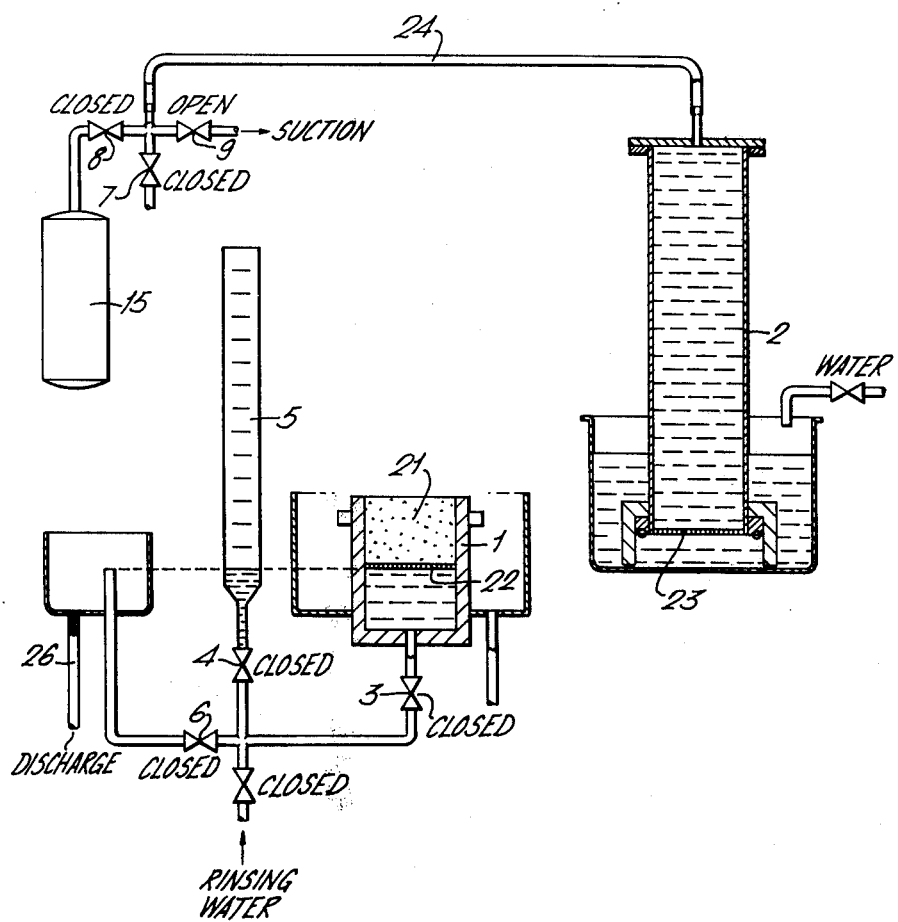

United States Patent [19]

V. Alfthan

[11] 4,024,754

[45] May 24, 1977

[54] METHOD AND APPARATUS FOR DETERMINATION OF DRAINABILITY OF MATERIAL IN SUSPENSION AND/OR STOCK FORM

[75] Inventor: Georg V. Alfthan, Helsinki, Finland

[73] Assignee: Oy Keskuslaboratorio-Central-laboratorium AB, Helsinki, Finland

[22] Filed: Mar. 18, 1976

[21] Appl. No.: 668,328

[30] Foreign Application Priority Data

Mar. 26, 1975   Finland ............................... 750931

[52] U.S. Cl. .................................................. 73/63
[51] Int. Cl.² ....................................... G01N 33/34
[58] Field of Search ............. 73/63, 61 R; 162/198, 162/263

[56] References Cited

UNITED STATES PATENTS

| | | | |
|---|---|---|---|
| 1,774,830 | 9/1930 | Green .................................... | 73/63 |
| 2,602,325 | 7/1952 | Campbell et al. ...................... | 73/63 |
| 2,734,378 | 2/1956 | Meyers ................................... | 73/63 |
| 3,688,563 | 9/1972 | Enarsson et al. ...................... | 73/63 |

Primary Examiner—Richard C. Queisser
Assistant Examiner—Joseph W. Roskos
Attorney, Agent, or Firm—Woodling, Krost, Granger & Rust

[57] ABSTRACT

A method is disclosed for determining the drainability of a material in suspension which comprises the steps of placing the suspension into a first container having a bottom with a multiplicity of small holes and an open top. The bottom of a second container which contains a measuring liquid is placed into the open top of the first container and this bottom, also, has small holes. The measuring liquid in the second container is pressurized to cause it to flow into and through the first container and through the material which was contained in suspension. The rate of flow of the fluid is a measure of the drainability of the material.

5 Claims, 9 Drawing Figures

METHOD AND APPARATUS FOR DETERMINATION OF DRAINABILITY OF MATERIAL IN SUSPENSION AND/OR STOCK FORM

This invention relates to a method and an apparatus for the determination of drainability of material in suspension and/or stock form, especially wood fiber pulp, so that water, preferably under pressure, is passed through a certain pulp layer, and the filtering resistance of the pulp in question is determined on the basis of the quantity of water flows through the layer per time unit.

Different apparatuses exist for the determination of drainability of material in suspension or stock form, especially wood fiber pulp. The most commonly used and best known in pulp and paper industry are Schopper Riegler apparatus and Canadian Standard Freeness Tester. These apparatuses are, however, very insensitive for fairly free pulps, for instance for pulp used in printing papers. Neither is it possible at all to use these apparatuses for testing the filtering of very finely refined pulp, for instance pulp for condenser paper is such finely refined pulp.

The object of this invention is to achieve an improvement in the above drawbacks and the characterizing features of the invention are set forth in the characterizing parts of the claims.

An apparatus according to the invention reacts very sensitively for instance to the important initial stage of pulp refining, at which stage the strength properties of pulp change very rapidly. By means of the apparatus, it is also possible to test the drainability of finely refined pulps.

So it is specific to the invention that a pulp sample to be tested is placed into a special cup with a bottom of perforated plate or wire, and a container with a bottom of perforated plate or wire, containing the water required in the test, is laid onto the cup. The pulp sample can first be allowed to drain freely for a certain time, before the actual draining in raised pressure is carried out by pressing the water by means of air pressure through the pulp layer formed on the bottom of the pulp cup.

By means of this arrangement, an apparatus has been obtained which operates very accurately and is very easy to use. The temperatures of the water and the test pressure are easy to control accurately. Fiber losses through the preforated plate or wire also remain small during the test when the draining is started by free drainage, and this also guarantees more accurate results.

Figure 3:
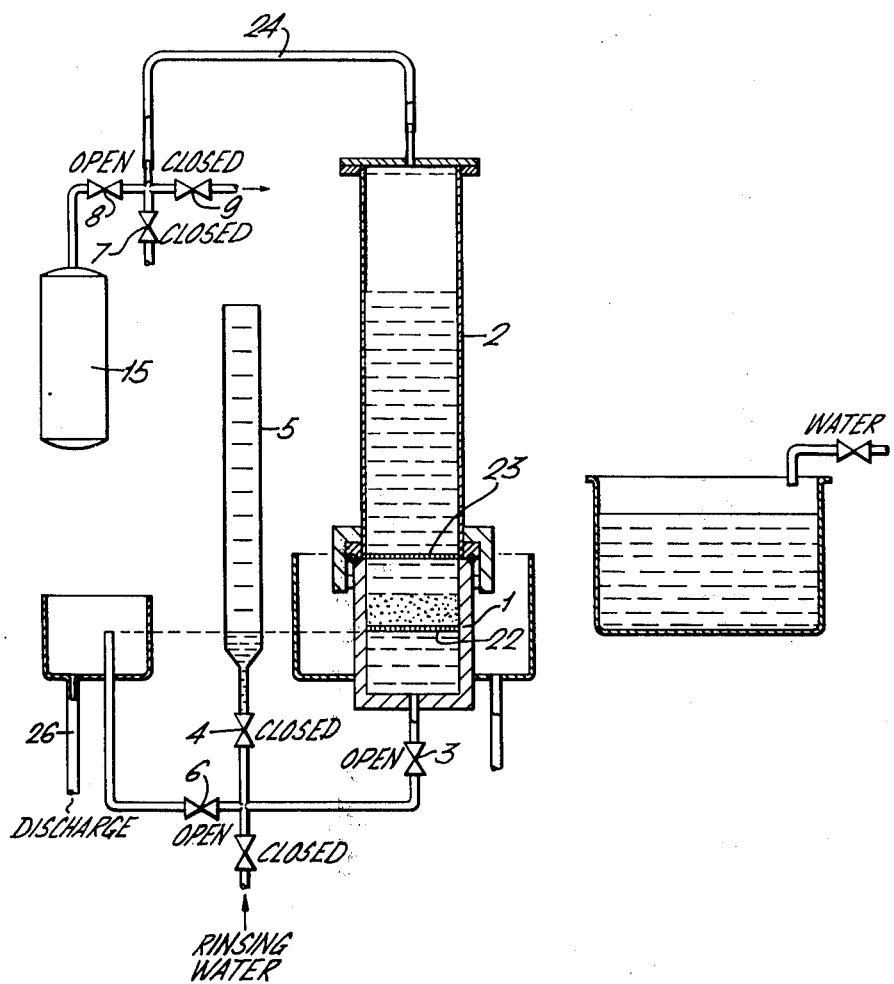
Figure 4:
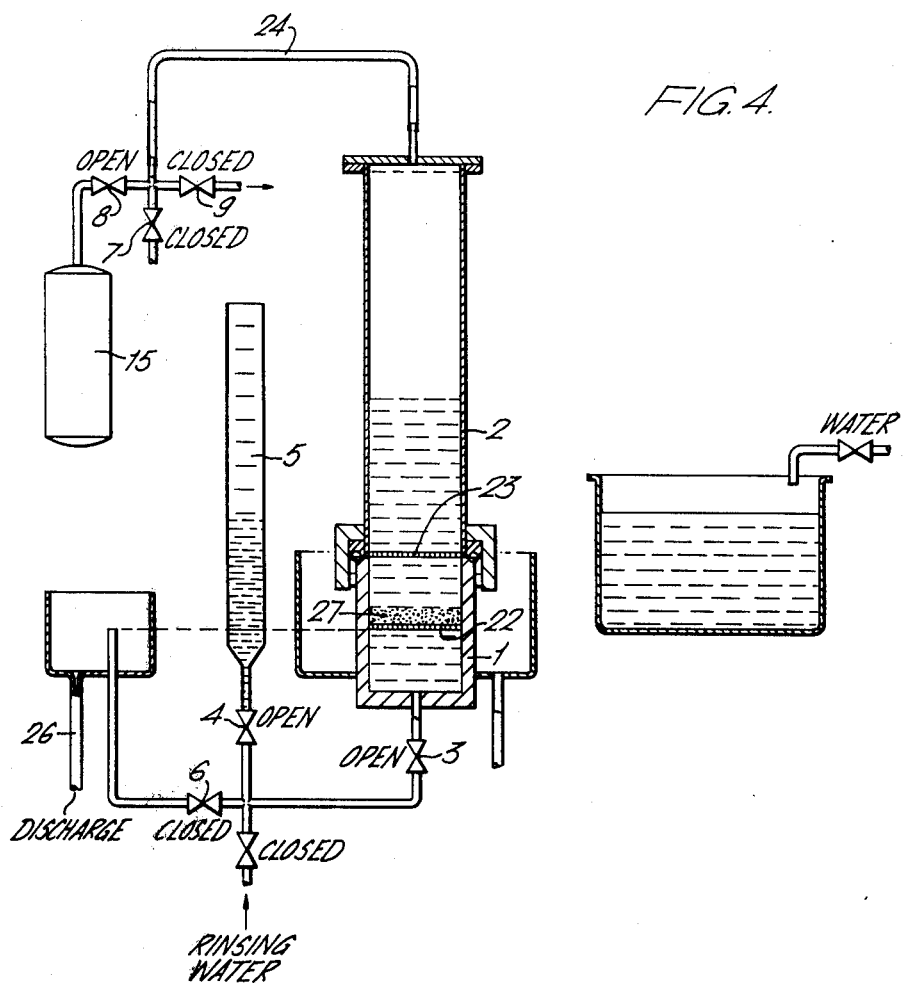
Figure 5:
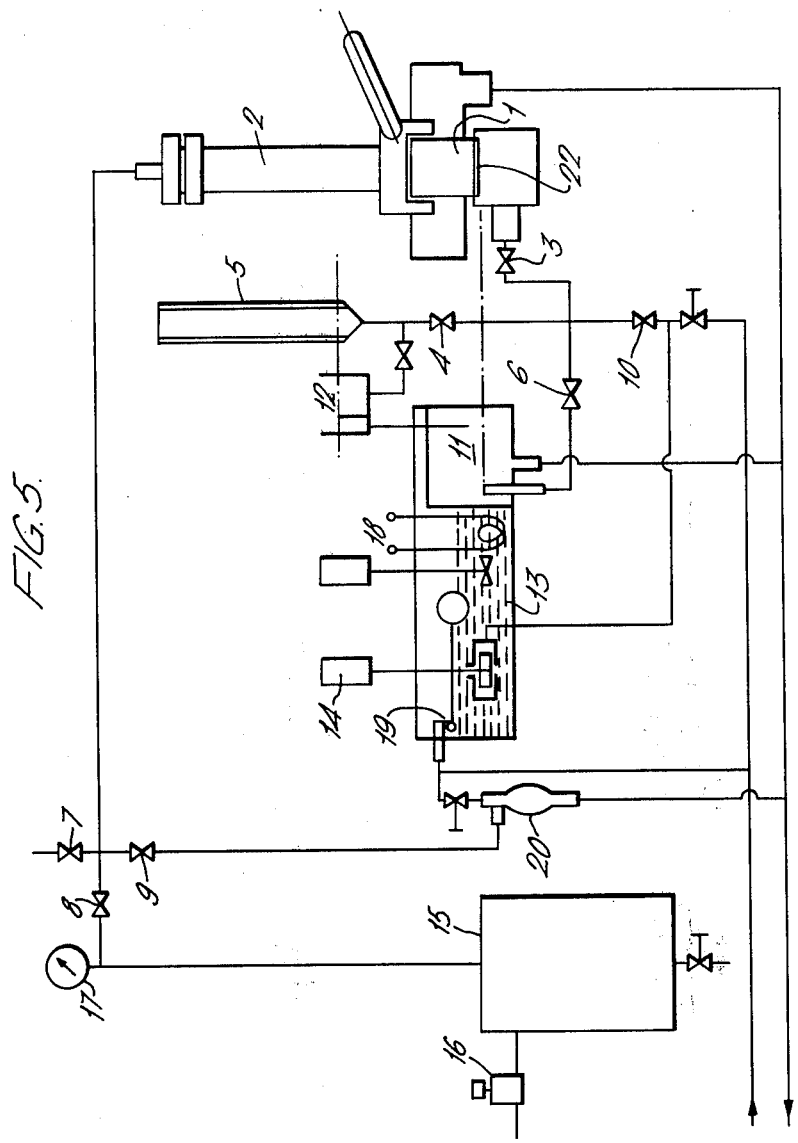

The invention is further described in the following with reference to the accompanying drawings in which FIG. 1-4 show in stages the determination of the drainability of a pulp by means of an apparatus according to the invention, FIG. 5 shows one circuit diagram developed for a practical embodiment of an apparatus according to the invention, and FIGS. 6-9 show graphs of values obtained by the method of the invention which values have been indicated as AS values, and values obtained by Schopper Riegler method presently in common use of which values degree indication SR° is used.

As shown in FIG. 1, sample suspension 21 is laid into sample cup 1, which is provided with bottom 22 of perforated plate or wire with small holes. The sample cup is of a size with certain measurements, for instance $\phi$56 mm and volume 170 ml. Water container 2 has a closed top and its lower part is provided with bottom 23 of perforated plate or wire with small holes. Water container 2 is filled with thermoregulated water in the way shown in FIGS. 1 and 5: The upper part of the water container can be connected with suction pump 20 by means of hose 24 and valve cntrol. During the suction stage, valves 7 and 8 are closed and valve 9 is open. When water container 2 is filled with water, valve 9 is closed and water container 2 is moved onto sample cup 1 and locked tightly with the cup. During the move, water cannot flow through the holes of bottom 23, not at least to any considerable degree, due to the small diameter of the holes. After this, three stages follow.

Figure 2:
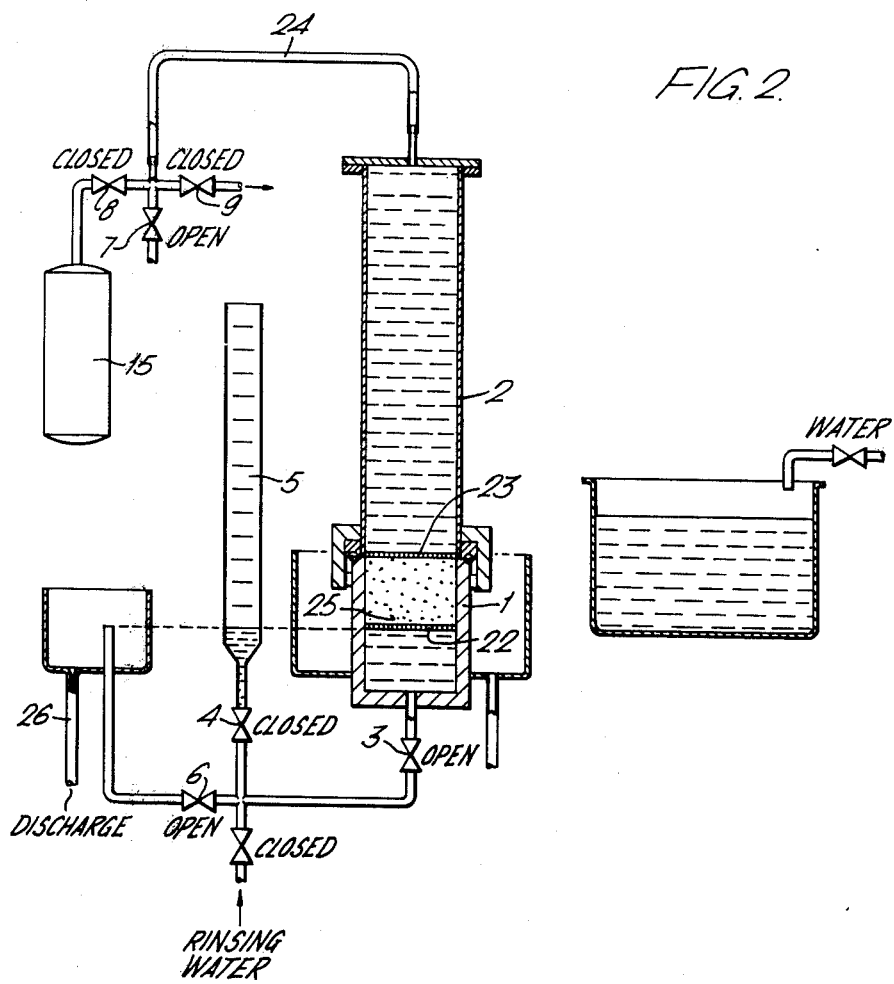

I stage: (FIG. 2)

The upper end of water container 2 is connected with the surrounding atmosphere by opening valve 7, and valve 3 of sample cup 1 is opened for a certain time, 5 seconds, for instance, so that thin, more compact layer 25 is formed of the suspension on the bottom of sample cup 1. The water coming from the cup is conducted to discharge pipe 26. During this stage, the drainage is free and the water is conducted to a discharge pipe for a certain time.

II stage: (FIG. 3)

Water container 2 is connected to compressed air chamber 15, and valve 3 is opened. Draining takes now place under relatively high pressure, 50–200 kPa, for instance, and water is allowed to flow from sample cup 1 to discharge pipe 26 for a certain time, 10–120 seconds, for instance. The time is restricted by closing valve 3.

III stages: (FIG. 4)

The water from sample cup 1 is conducted through valve 4 into measuring chamber 5 by opening valves 3 and 4. Water container 2 is still connected with compressed air chamber 15. Valve 3 is open for a certain time, 15–125 seconds, for instance, The water coming during this time from sample cup 1 is measured in measuring chamber 5. The quantity in milliliters observed is the measurement of the drainability of the sample. Water is therefore forced under a certain pressure through a certain pulp layer 27, and the quantity of water flowing per time unit is measured. The more water per time unit passes through the pulp layer, the smaller the drainage resistance is and the better the pulp drains.

In the above, the draining rate is measured by measuring the quantity of water flown per time unit. Of course it is possible for the test to measure the time a certain water quantity takes to flow into measuring chamber 5, with which time the flow rate is inversely proportional. Other quantities affecting the test result, such as the times mentioned at stage I-II, the pressure, the volume of the containers, etc. are constant at least during the same test and/or test series, but they can also be varied for different pulp qualities, for instance.

In the circuit diagram of FIG. 5, there is sample cup 1 provided with bottom 22 of perforated plate. The sample cup acts at the same time also as a measurement cup. The volume of the sample cup is 170 ml, for instance. Reference number 2 indicates a water container with a bottom of perforated plate and having a volume of 2000 ml, for instance. Main valve 3 of sample cup 1 controls the filtering times. The components of the circuit diagram are further indicated as follows: inlet valve 4 of measurement chamber 5; measurement chamber 5; valve 6 connecting sample cup 1 to overlow 11; valve 7 connecting the upper part of water container 2 to open air; valve 8 connecting the upper part of water container 2 to chamber 15 with constant pressure; valve 9 connecting the upper part of water container 2 to suction pump 20; valve 10 connecting sample cup 1 to rinsing pump 14; overflow 11 of sample cup 1; overlow 12 of measuring chamber 5 for zero positioning: thermoregulated water basin 13 from which water container 2 is filled by drawing suction into it by means of suction pump 20 before the test; rinsing pump 14 of sample cup 1, and its motor; chamber 15 with constant pressure; pressure regulating valve 16; pressure meter 17; thermostat 18; float valve 19 and suction pump 20. The timing of valves 3, 4, 6, 7, 8, 9 and 10 is best to control automatically.

Figure 6:
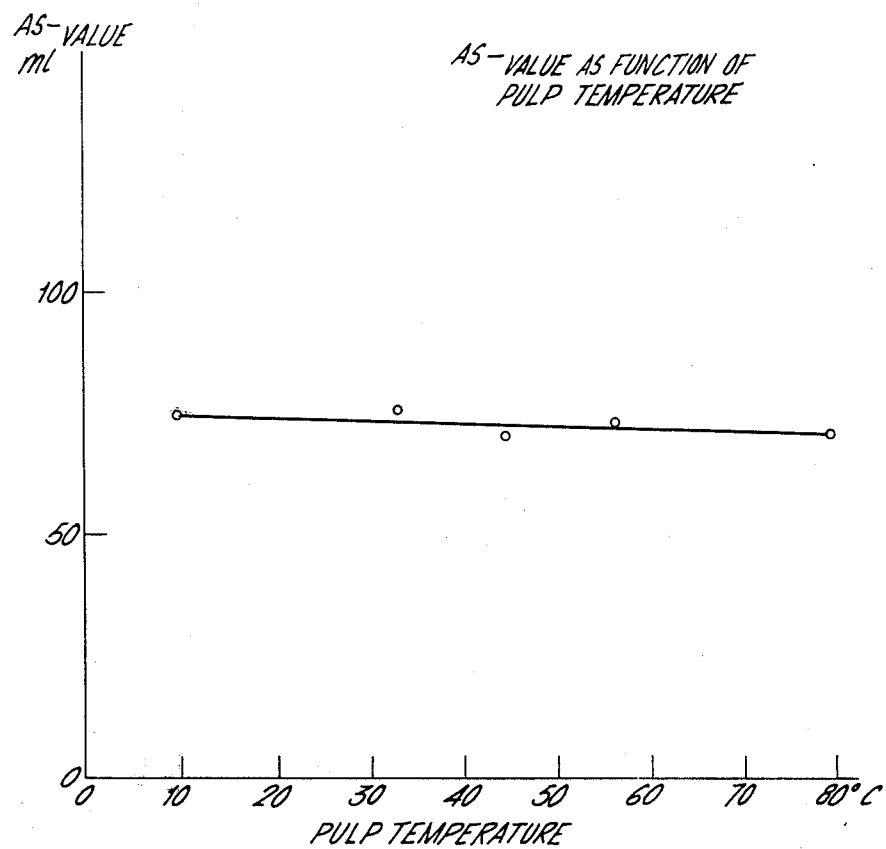
Figure 7:
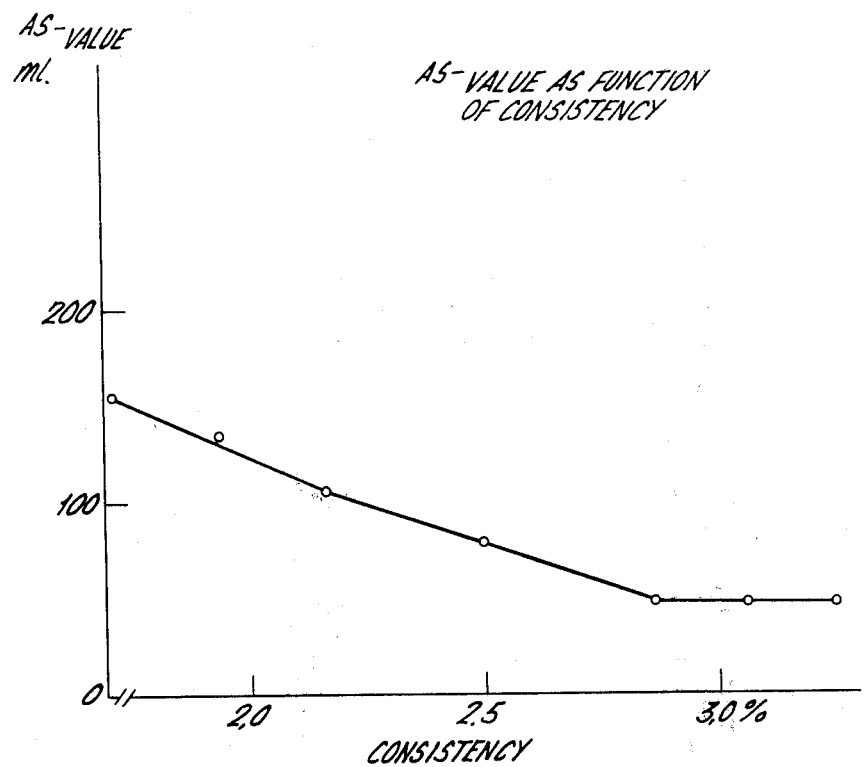

FIG. 6 shows drainage values of a ground pulp at different temperatures. It shows that the temperature range of 10°–80° C. has hardly any effect on the AS values obtained. So the method according to the invention is hardly sensitive at all to the temperatures of the pulp sample. This is of great importance, particularly in mill conditions, because it makes the determination much faster and simpler.

The method is insensitive also to the consistency of the sample within a certain range which is somewhat dependent on the quality of the pulp. For instance in the case shown in FIG. 7, the insensitive range is on both sides of 3%. The matter concerns slightly refined sulfite pulp.

It is normal that in certain cases this makes the determination of values easier.

Figure 8:
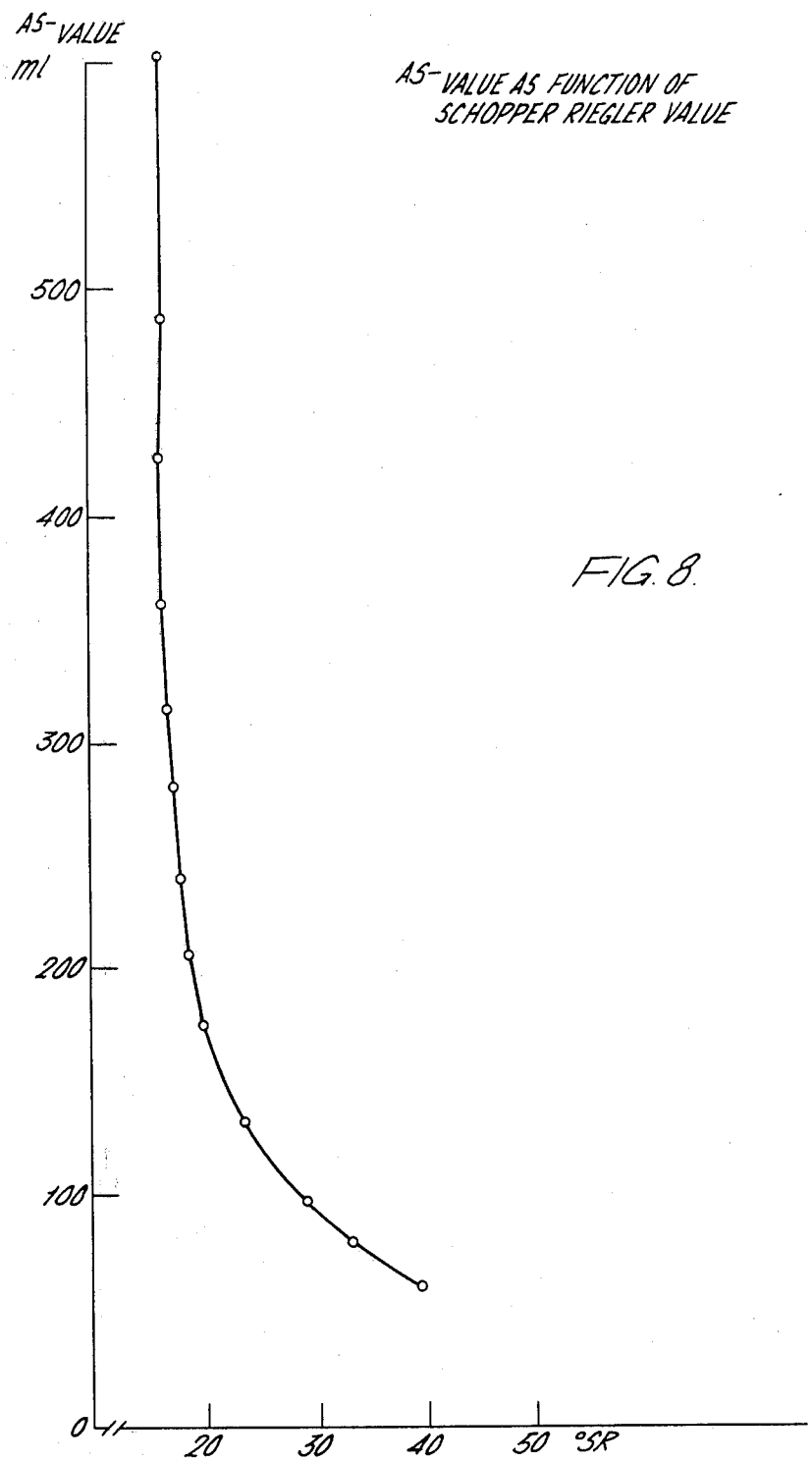

By means of the method according to the invention, it is possible to watch the refining of pulp at the initial stage of the refining with an accuracy that has not been possible before if compared to other methods used previously. This initial stage is important because in the beginning of the refining, the important properties of pulp, such as strength, develop rapidly. When compared to conventionally used filtering measurement, Schopper Riegler degree the method according to the invention is of the magnitude of about 100 times more sensitive for instance within the range of 16° – 20° SR, as can be seen from FIG. 8. FIG. 8 shows values with a sulfate pulp which has been refined to various beating degrees and measured both as AS values and in SR degrees.

Figure 9:
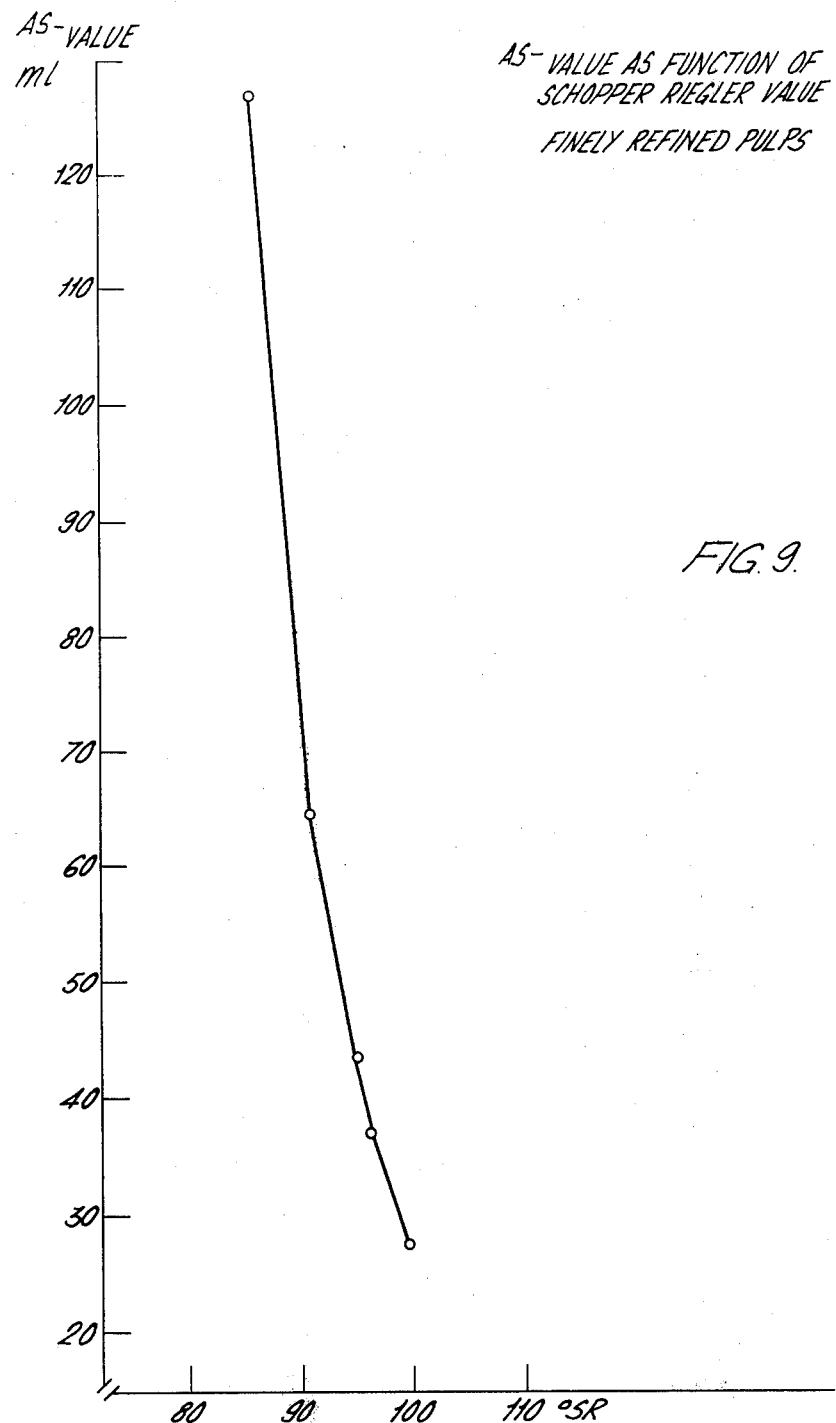

FIG. 9 shows results obtained by the method of the invention and corresponding SR degrees with a finely refined sulfate pulp. Schopper Riegler method is very uncertain within these ranges and it cannot be used over 95°SR. By using suitable consistency and time program, it is possible to test the drainage properties of pulps with great accuracy by means of the method of the invention, however finely refined the pulps are.

I claim:

1. The method of determining the drainability of material in suspension and or stock form, especially wood fiber pulp, comprising the steps of placing a suspension of the material in water into a first container having a bottom with a multiplicity of small holes and an open top, placing the bottom of a second container which contains a measuring liquid into the open top of said first container, said bottom of said second container having small holes, and pressurizing the measuring liquid in said second container to cause it to flow into said first container, through the material and out of said container through the small holes in the botom of said first container, the rate of flow of said measuring liquid being a measure of the drainability of the material.

2. The method according to claim 1, characterized in that the water in the material is first allowed to drain freely through the bottom of the first container and under a relatively small pressure before the measuring liquid in the second container is pressurized.

3. The method according to claim 1, characterized in that the measuring liquid in the second container is brought under a desired pressure by means of compressed air by conducting compressed air to the upper part of the second container.

4. The method according to claim 3, characterized in that the entire quantity of measuring liquid used in the determination of the filtering properties of the material is placed into the second container at the same time.

5. Apparatus for determining the drainability of material in suspension and/or stock form, especially wood fiber pulp, comprising a first container having a bottom with a multiplicity of small holes and an open top, a second container adapted to contain a measuring liquid and having a closed top and a bottom having small holes, means tightly connecting said bottom of said second container into the open top of said first container and means for pressurizing said closed top of said second container.

* * * * *